US010100313B2

(12) United States Patent
Lennon-Dumenil et al.

(10) Patent No.: US 10,100,313 B2
(45) Date of Patent: Oct. 16, 2018

(54) USE OF MCOLN-1 MODULATORS TO REGULATE CELL MIGRATION

(71) Applicants: INSTITUT CURIE, Paris (FR); INSERM (INSTITUT NATIONAL DE LA SANTE ET DE LA RECHERCHE MEDICALE), Paris (FR)

(72) Inventors: Ana-Maria Lennon-Dumenil, Paris (FR); Pablo Vargas, Paris (FR); Marine Bretou, Paris (FR)

(73) Assignees: INSTITUT CURIE, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 15/116,848

(22) PCT Filed: Feb. 10, 2015

(86) PCT No.: PCT/EP2015/052744
§ 371 (c)(1),
(2) Date: Aug. 5, 2016

(87) PCT Pub. No.: WO2015/118167
PCT Pub. Date: Aug. 13, 2015

(65) Prior Publication Data
US 2017/0145423 A1    May 25, 2017

(30) Foreign Application Priority Data

Feb. 10, 2014 (EP) .................................. 14305172

(51) Int. Cl.
*A61K 39/00* (2006.01)
*C12N 15/113* (2010.01)
*C12N 5/0784* (2010.01)
*A61K 39/39* (2006.01)

(52) U.S. Cl.
CPC ...... *C12N 15/1138* (2013.01); *A61K 39/0011* (2013.01); *A61K 39/39* (2013.01); *C12N 5/0639* (2013.01); *A61K 2039/57* (2013.01); *C12N 2310/14* (2013.01); *C12N 2500/14* (2013.01); *C12N 2501/50* (2013.01); *C12N 2517/02* (2013.01)

(58) Field of Classification Search
CPC ... C12N 5/0639; A61K 39/0011; A61K 39/00
USPC ...................................... 424/277.1
See application file for complete search history.

(56) References Cited

U.S. PATENT DOCUMENTS

2003/0064363 A1    4/2003  Goldin et al.
2016/0298082 A1*  10/2016  Henco ................ A61K 35/15

FOREIGN PATENT DOCUMENTS

WO    WO 99/00137    1/1999
WO    WO 99/62537    12/1999

OTHER PUBLICATIONS

Gura (Science. 1997; 278: 1041-1042).*
Dennis (Nature. Aug. 7, 2006; 442: 739-741).*
Shen et al. (Nature Communications, Mar. 13, 2012, 3: 731, pp. 1-11).*
Database Chemical Abstracts [Online] Chemical Abstracts Service, Accession No. 116:104256, Liu et al. "The enhancing effect of calcium ionophore A23187 on the accessory function of mouse dendritic cells", 1991, XP-002047046, p. 1.
Written Opinion in International Application No. PCT/EP2015/052744, dated Apr. 14, 2015, pp. 1-6.

* cited by examiner

*Primary Examiner* — Yan Xiao
(74) *Attorney, Agent, or Firm* — Saliwanchik, Lloyd & Eisenschenk

(57) ABSTRACT

The present invention relates to the use of modulators of Mcoln-1 for modulating cell migration, in particular the migration of dendritic cells and tumor cells, especially for antitumoral vaccination, autoimmune disease treatment, and metastasis prevention.

5 Claims, 6 Drawing Sheets
Specification includes a Sequence Listing.

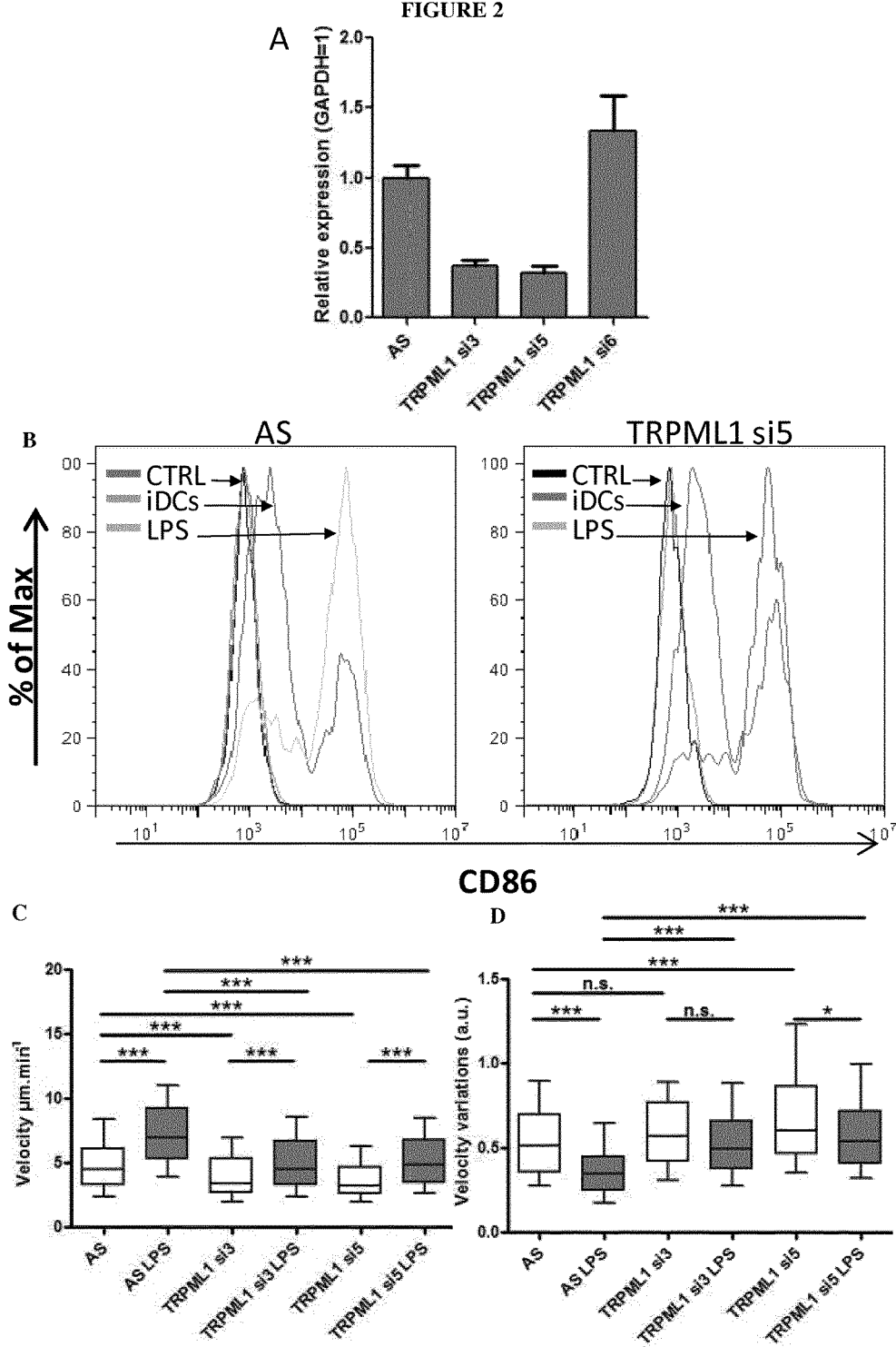

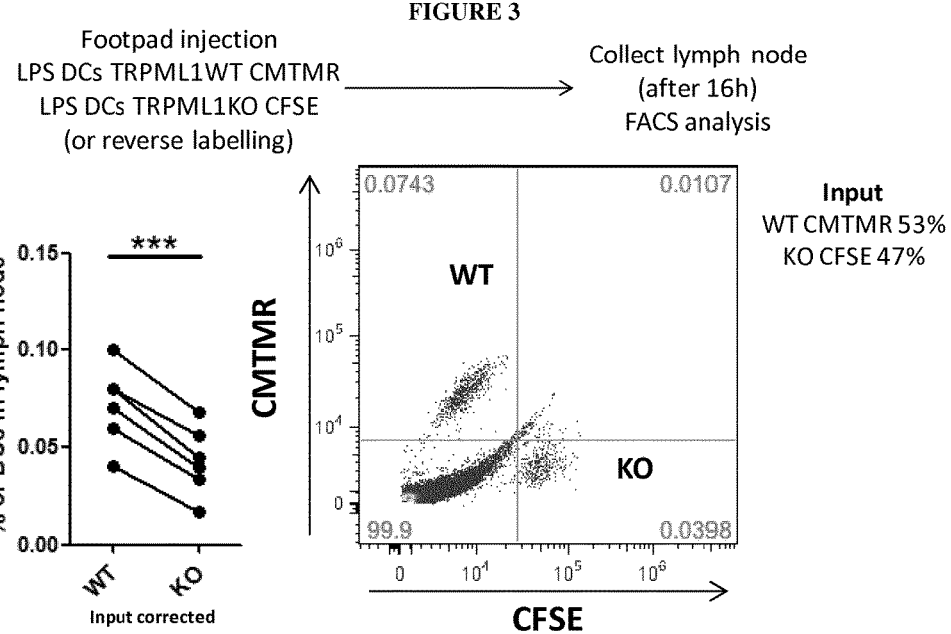
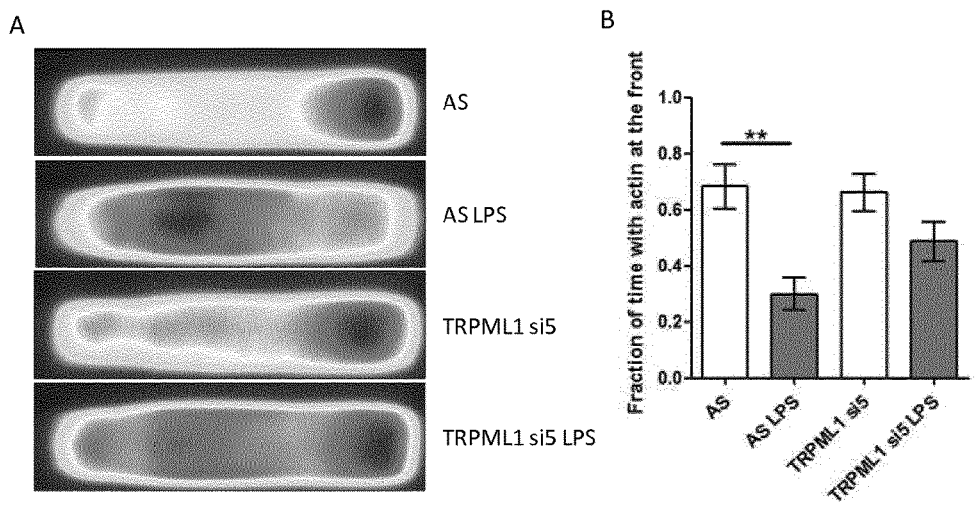

USE OF MCOLN-1 MODULATORS TO REGULATE CELL MIGRATION

CROSS-REFERENCE TO RELATED APPLICATION

This application is the U.S. national stage application of International Patent Application No. PCT/EP2015/052744, filed Feb. 10, 2015.

The Sequence Listing for this application is labeled "Seq-List.txt" which was created on Jul. 19, 2016 and is 2 KB. The entire content of the sequence listing is incorporated herein by reference in its entirety.

FIELD OF THE INVENTION

The present invention relates to the medicine, in particular the oncology and to autoimmune disease treatment.

BACKGROUND OF THE INVENTION

Immune activation induces activation and maturation of dendritic cells. Dendritic cells (DCs) are a part of the immune system that act as antigen-presenting cells. They process antigen material and present it on their cell surface. The antigen material may be from microbial organisms such as viruses or bacteria or from self antigens.

Immature DCs become activated after detecting a microbial antigen. The antigen protein is degraded by DCs and the fragments are presented on their surface in association with Major Histocompatibility (MHC) molecules. Upon activation, DCs migrate to the lymph nodes and present these antigens to T lymphocytes. This is the first step of the adaptive immune response.

Cancer immunotherapy aims at eliciting an immune response directed against tumor antigens. One approach is through vaccination by the provision of an antigen together with an adjuvant to elicit therapeutic T cells in vivo. DCs have been used in this context due to their high antigen presenting property, which makes them the natural agents for tumor-associated antigen delivery. In particular, ex vivo generated DCs can be loaded with antigens and re-infused to the patient. Alternatively, antigens can be targeted to DCs in vivo without need for ex vivo cell manipulations (Palucka & Bachereau, Nat Rev Cancer, 2012, 12, 265; Tacken et al, Nat Rev Immunol, 2007, 7, 790). However, one limitation is that the DCs injected to patients migrate inefficiently to lymphoid organs, a process required to trigger antitumoral immunity.

DCs have several functions in innate and adaptive immunity. In particular, there is increasing evidence that DCs induce antigen-specific unresponsiveness or tolerance in central lymphoid organs and in the periphery. In particular, immature DCs induce tolerance either through T cell deletion or by inducing the expansion of regulatory and/or suppressor T cells. Accordingly, they have tolerogenic properties that can be used in the treatment of autoimmune diseases such as diabetes, arthritis and autoimmune myocarditis (Steinman et al, Annu Rev Immunol, 2003, 21, 685-711; Xiao et al, J Immunother, 2006, 29, 465-471; van Duivenvoorde et al, J Immunol, 2007, 1506-1515; Valaperti et al, Vaccine, 2013, 31, 4802-4811; Tbarozzi et al, Clin Exp Immunol, 2012, 171, 135-146). Therefore, in this context, it might be advantageous to enhance the migration of DCs to the lymph nodes, in particular of immature DCs.

DCs are not the only cells for which migration is essential. Indeed, cell migration is a central process for embryonic development, wound healing, and metastasis.

An understanding of the mechanism by which cells migrate may lead to the development of novel therapeutic strategies for controlling, for example, invasive tumoral cells. For instance, invasion into the lymphatic system allows the transport of tumor cells to regional and distant lymph nodes and, ultimately, to other parts of the body. Cancer cells may spread to lymph nodes near the primary tumor and then disseminate. This is the most common route of metastasis for carcinomas. Therefore, it might be advantageous to decrease or prevent cancer cell migration in order to avoid metastasis. However, attempts to prevent cancer spreading by inhibiting cell migration have not succeeded so far.

Interestingly, cancer cells share migration properties with DCs. More particularly, podosomes or invadosomes are cylindrical, actin-rich structures that display a polarized pattern of distribution in migrating cells. Their primary purpose is connected to cellular motility and invasion. Many different specialized cells exhibit these dynamic structures such as invasive cancer cells, and certain immune cells such as DCs (Gimona et al, Current Opinion in Cell Biology 20 (2): 235-41).

SUMMARY OF THE PRESENT INVENTION

The inventors discovered an unexpected role of lysosomes in the regulation of DC migration. They found that DC activation increases their migration and persistence by triggering the formation of a patch of actin cables located at the DC rear and that lysosomes are tightly apposed to these actin structures in migrating DCs and have shown that they have a role in the regulation of actin dynamics and DC migration. Indeed, by blocking lysosomal biogenesis and secretion (by silencing of TFEB, a transcription factor that controls lysosome biogenesis), they observed a DC migration defect associated with the loss of actin polymerization at the rear of DCs, suggesting that lysosome function and/or secretion control the organization of actin distribution and DC migration. More particularly, they found that the lysosomal calcium channel Mcoln-1 controls DC migration, either ex vivo or in vivo, i.e., DC migration is decreased when Mcoln-1 is inhibited and, on the opposite, is enhanced when Mcoln-1 is activated, in particular in immature DCs. Mcoln-1 is required for actin polymerization at the cell rear and for fast and persistent DC migration.

The present invention relates to a molecule modulating Mcoln-1 for use for modulating cell migration.

In a first aspect, the modulating molecule is an activator of Mcoln-1, which therefore enhances cell migration. Preferably, the cells are DCs.

The Mcoln-1 activator can be used in vaccination, in particular antitumoral vaccination (in particular with mature DCs), or to treat an autoimmune disease (in particular with immature DCs), and to treat infection (in particular with mature DCs).

In particular, the molecule modulating Mcoln-1 can be an activator selected from the group consisting of an antibody directed against Mcoln-1 and having an agonist activity, or a small molecule or a peptide activating Mcoln-1 such as ML-SA1, SF-22 and SF-51.

In a second aspect, the modulating molecule is an inhibitor of Mcoln-1, which therefore impairs cell migration. Preferably, the cells are tumor cells.

Therefore, the Mcoln-1 inhibitor can be used to treat cancer, in particular to prevent or decrease metastasis.

In particular, the molecule modulating Mcoln-1 is an inhibitor or blocker selected from the group consisting of an antibody directed against Mcoln-1 and having an antagonist activity, an oligonucleotide inhibiting or decreasing the expression of Mcoln-1 such as antisense, siRNA or shRNA, an aptamer specific to Mcoln-1 and having an antagonist activity, a Calcium channel blocker specific to Mcoln-1, a peptide or a small molecule inhibiting or blocking Mcoln-1 such as ML-SI1, ML-SI2 and ML-SI3, Sphingomyelins, or verapamil.

Finally, the present invention relates to a method to identify or screen for a molecule capable of modulating cell migration, comprising determining the effect of a molecule on the activity of Mcoln-1 and selecting the molecule if it increases or decreases the activity of Mcoln-1. Optionally, it may further comprise a step of determining the effect of the selected molecule on cell migration or velocity and selecting the molecule(s) that increase or decrease cell migration or velocity.

DETAILED DESCRIPTION OF THE INVENTION

Mcoln-1 is also currently named mucolipin-1 or TRPML-1 (Transcient Receptor Potential Cation Channel, Mucolipin subfamily). It is a $Ca^{2+}$ channel localized in late endosomes and lysosomes. It belongs to the small family of the TRPML channels (includes 3 members), a subgroup of the large protein family of TRP ion channels. Mcoln-1 deficiency causes type IV mucolipidosis.

Mcoln-1 is described in several databases, namely UniProt ID No Q9GZU1 and Gene ID No 57192. Reference sequences are disclosed in Genbank under NM_020533 for mRNA and NP_065394 for protein.

Briefly, the inventors identified Mcoln-1 as a key factor for the control of cell migration, in particular DC migration. More specifically, cell migration is decreased when Mcoln-1 is inhibited and, on the opposite, is enhanced when Mcoln-1 is activated, in particular in immature DCs. They demonstrated that Mcoln-1 is required for actin polymerization at the cell rear and for fast and persistent migration of DCs. They also demonstrate the ability of Mcoln-1 inhibitor to decrease the tumoral cell migration.

Therefore, Mcoln-1 is a good therapeutic target for controlling cell migration. In addition, because Mcoln-1 localizes to lysosomes, its luminal domains are directly accessible to extracellular compounds. Accordingly, there is no absolute need for Mcoln-1 modulators to be cell-permeable. Finally, as Mcoln-1 disruptive mutations cause Type IV mucolipidosis, which is a non-lethal lysosomal storage disease, treatments with Mcoln-1 modulators will have no or limited toxicity.

Then, the present invention relates to a Mcoln-1 modulator for use for modulating cell migration, to the use of a Mcoln-1 modulator for the preparation of a drug that modulates cell migration, or a method to modulate cell migration, wherein a Mcoln-1 modulator is administered to a subject. In a preferred embodiment, the Mcoln-1 modulator may be selective with respect to Mcoln-1. That means that the Mcoln-1 modulator has a greater efficacy on TRPML-1 in comparison to TRPML-2 and/or TRPML-3 (for instance by a factor of at least 10, 100 or 1000).

In a first aspect, the present invention relates to a Mcoln-1 activator that is capable to increase or enhance cell migration in vivo. In this context, the present invention relates to a Mcoln-1 activator to be used to increase or enhance cell migration, to the use of a Mcoln-1 activator for the preparation of a drug that increases or enhances cell migration, or a method to increase or enhance cell migration, wherein a Mcoln-1 activator is administered to a subject, preferably a therapeutically effective amount thereof.

The Mcoln-1 activator can be used for treating any disease or disorder that can have a therapeutic benefit from an increased or enhanced cell migration. By "increase" or "enhance" is intended to refer to a cell migration that is increased by at least 10, 20, 30, 40 or 50% as compared to a cell migration measured in the absence of the Mcoln-1 activator. By cell migration can be intended cell velocity, the percentage of migrating cells or a combination of these two criteria. Cell migration can be determined by any method known by the person skilled in the art, for instance by a method using micro-channel as detailed in Faure-Andre et al for measuring the velocity (Faure-Andre et al, 2008, Science, 322, 1705-10).

In a preferred aspect, the cell is a DC. In a very specific aspect, it can be an immature DC. Indeed, the inventors clearly demonstrate that Mcoln-1 activators can give immature DCs the capacity to migrate similarly to mature DCs while keeping their immature status.

As DCs are sentinels of the immune system and are used in many vaccination protocols, in particular in the context of antitumoral vaccination, DC migration might be increased by treating the cells with a Mcoln-1 activator. Accordingly, the present invention relates to a Mcoln-1 activator for use in vaccination, in particular for antitumoral vaccination, or to the use of a Mcoln-1 activator for the preparation of a vaccine, preferably an antitumoral vaccine. Due to the capacity of Mcoln-1 activators to increase the migration of DCs, it may overcome the admitted limitation of inefficient DC migration to lymphoid organ during antitumoral vaccination.

The present invention relates to a Mcoln-1 activator for use for treating cancer in combination with an antitumoral vaccine or to the use of a Mcoln-1 activator for the manufacture of a drug for treating cancer in combination with an antitumoral vaccine. In particular, said antitumoral vaccine comprises tumor antigens, especially DCs charged with tumor antigens or encoding tumor antigens. It also relates to a Mcoln-1 activator for improving the therapeutic efficiency of an antitumoral vaccine.

This is particularly true in the context of antitumoral vaccination. In this context, tumor antigen(s) is/are administered to the patient. They can be either previously charged on DCs ex vivo or administered directly.

Tumor antigens useful for antitumoral vaccination are well known in the art. A non-exhaustive list thereof includes carcinoembryonic antigen (CEA), MAGE (i.e., 1, 2, 3, or 12), BAGE, GAGE, NY-ESO-1, SSX, Gp100, Melan-A/Mart-1, Tyrosinase, Mammaglobin-A, p53, prostate specific antigen (PSA), human epidermal growth factor receptor-2 (HER2/neu), livin, survivin, alpha-fetoprotein (AFP), cancer antigen or carbohydrate antigen (CA 125, CA 15-3 and CA 19-9), β-catenin-m, β-actin/4/m, Myosin/m, HSP70-2/m, HLA-A2-R170J, and mucin-1 (MUC-1). In addition, tumor lysates or apoptotic debris can be used as antigens. For review, Even-Desrumeaux et al, 2011, Cancers, 3, 2554-2596; Buonaguro et al, 2011, Clin Vaccine Immunol, 18, 23-34.

Several vaccine strategies have been developed and could be summarized in the following groups: direct administration of tumor antigens (optionally, fused to a DC receptor), administration of tumor antigens charged on DCs, or administration of DCs transfected by nucleic acids encoding tumor antigens. DC-based vaccines represent one of the most promising strategies. For review, Tacken et al, 2007, Nature Reviews Immunology, 7, 790-802.

In a particular aspect, DCs are autologous DCs from the patient to be treated. Therefore, the present invention relates to a pharmaceutical composition comprising autologous DCs treated by a Mcoln-1 activator or to a kit comprising DCs and a Mcoln-1 activator. Optionally, it may further comprise a vaccine adjuvant.

In another particular aspect, the present invention relates to a pharmaceutical composition comprising a tumor antigen and a Mcoln-1 activator or to a kit comprising a tumor antigen and a Mcoln-1 activator. Optionally, it may further comprise a vaccine adjuvant.

In a distinct therapeutic use, a Mcoln-1 activator can be used to treat or prevent an autoimmune disease or disorder. Indeed, as a Mcoln-1 activator increases or enhances DC migration while it does not up-regulate co-stimulatory molecules, it could be of interest to induce tolerance in the context of immunity. Indeed, it has been shown for instance that DC injection in diabetic mice inhibits autoimmunity (Richer et al, PLos One, 7, e31153). Similarly, encouraging results have been observed in diabetes, arthritis and autoimmune myocarditis (Steinman et al, Annu Rev Immunol, 2003, 21, 685-711; Xiao et al, J Immunother, 2006, 29, 465-471; van Duivenvoorde et al, J Immunol, 2007, 1506-1515; Valaperti et al, Vaccine, 2013, 31, 4802-4811; Tbarozzi et al, Clin Exp Immunol, 2012, 171, 135-146). Therefore, treatment with a Mcoln-1 activator can increase the migratory properties of immature DCs, thereby inducing tolerance and reducing or preventing autoimmune reactions.

Accordingly, the present invention relates to a Mcoln-1 activator for use to treat an autoimmune disease or disorder, or for the use of a Mcoln-1 activator for the preparation of a drug for treating an autoimmune disease or disorder. It also relates to a method to treat an autoimmune disease or disorder comprising administering a therapeutically effective amount of a Mcoln-1 activator.

For instance, the autoimmune disease or disorder is selected from the non-exhaustive group comprising type I diabetes, rheumatoid arthritis, autoimmune cardiomyopathy, acute disseminated encephalomyelitis, Addison's disease, Alopecia areata, ankylosing spondylitis, antiphospholipid syndrome, Barth syndrome, Crohn's disease, Graves' disease, autoimmune hemolytic disease, autoimmune hepatitis, IgA nephropathy, immune, idiopathic thrombocytopenic purpura (ITP), inflammatory bowel disease, irritable bowel syndrome, Kawasaki disease, lupus erythematosus systemic, microscopic polyangiitis, multiple sclerosis, myasthenia Gravis, Myositis, pelvic inflammatory disease, pemphigus, polymyalgia rheumatica, primary biliary cirrhosis, primary sclerosing cholangitis, psoriasis, rheumatic fever, sarcidosis, scleroderma, Sjogren's syndrome, thyroiditis, ulcerative colitis, autoimmune lymphoproliferative syndrome, autoimmune peripheral neuropathy, autoimmune pancreatitis, autoimmune polyendocrine syndrome, autoimmune progesterone dermatitis, autoimmune urticaria, autoimmune uveitis, Behçet's disease, celiac disease, cold agglutinin disease, dermatomyositis, eosinophilic fasciitis, gastrointestinal pemphigoid, Goodpasture syndrome, Guillain Barré syndrome, Hashimoto's encephalopathy, Hashimoto's thyroiditis, mixed connective tissue disease, polymyositis, psoriatic arthritis, Reiter's syndrome, and vasculitis such as Churg-Strauss syndrome, microscopic polyangiitis, and Wegener granulomatosis. In a particular aspect, the autoimmune disease is selected from the group consisting of type I diabetes, rheumatoid arthritis and autoimmune cardiomyopathy.

The present invention also relates to a Mcoln-1 activator for use to treat an infectious disease, or to the use of a Mcoln-1 activator for the preparation of a drug for treating an infectious disease. It also relates to a method to treat an infectious disease comprising administering a therapeutically effective amount of a Mcoln-1 activator. The disease can be a viral infection or a bacterial infection.

In a more general aspect, the present invention relates to a Mcoln-1 activator for use as a drug or to the use of a Mcoln-1 activator for the manufacture of a drug, or a pharmaceutical composition comprising a Mcoln-1 activator. The Mcoln-1 activator can be used in combination with an additional drug.

The Mcoln-1 activator can be any molecule capable of increasing Mcoln-1 activity. Mcoln-1 activity can be determined by any method known by the person skilled in art; for instance, see Shen et al., 2012, Nat. Comm., 3:731. Preferably, a Mcoln-1 activator is a molecule capable of increasing the activity of Mcoln-1 by at least 10, 20, 30, 40 or 50% when compared to the activity in absence of the molecule. The terms "activator" and "agonist" can be used and are interchangeable. The activity can be measured for instance by measuring the calcium permeability.

The Mcoln-1 activator can be selected from the group consisting of an antibody directed against Mcoln-1 and having an agonist activity, and a small molecule or peptide activating Mcoln-1 such as ML-SA1, SF-22 and SF-51.

Small molecules refer in particular to small organic molecules with a molecular mass <1000 Da. Small molecules and other drug candidates can readily be obtained, for example, from combinatorial and natural product libraries and using methods known in the art, or screening methods for their Mcoln-1 agonizing activity. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) and MycoSearch (NC), or are readily producible by methods well known in the art. Furthermore, random peptide libraries, consisting of all possible combinations of amino acids, attached to a solid phase or in solution, may also be used to identify peptides that act as agonists.

Activators can be selected from the group consisting of ML-SA1 (Sigma-Aldrich Cat # SML0627; Tocris Bioscience Cat #4746), SF-22 (5-chloro-N-(2-piperidin-1-ylphenyl)thiophene-2-sulfonamide) and SF-51 (2-[2-oxo-2-(2,2,4-trimethylquinolin-1-yl)ethyl]isoindole-1,3-dione).

The antibody directed against Mcoln-1 and having an agonist activity can be for instance prepared by the following method comprising immunizing a non-human mammal with a composition comprising human Mcoln-1 or an immunogenic fragment thereof; optionally selecting an antibody that binds to Mcoln-1 or the immunogenic fragment thereof, and selecting an antibody that increases the activity of Mcoln-1. The preparation of monoclonal or polyclonal antibodies is well known in the art, and any of a large number of available techniques can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to desired polypeptides. Also, transgenic mice, or other organisms such as other mammals, may be used to express humanized, chimeric, or similarly modified antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

As used herein, the terms "antibody" and "immunoglobulin" have the same meaning and are used indifferently in the present invention. The term "antibody" refers to immunoglobulin molecules and immunologically active portions of immunoglobulin molecules, i.e., molecules that contain an antigen-binding site that immunospecifically binds an antigen. Antibodies include any kind of antibodies, preferably monoclonal. They can be for instance IgG (immunoglobulin G) or VHH (heavy chain variable domain antibody from camelids). Antibodies fragments or derivatives thereof include Fab, Fab', F(ab')2, scFv, (scFv)2, dAb, complementarity determining region (CDR) fragments, linear antibodies, single-chain antibody molecules, minibodies, diabodies, and multispecific antibodies formed from antibody fragments.

More generally, the present invention further relates to a method for selecting or identifying a molecule suitable for increasing or enhancing cell migration, in particular DC migration, comprising determining the effect of a molecule on the activity of Mcoln1 and selecting the molecule if it increases the activity of Mcoln1. The method may further comprise a step of determining the effect of the selected molecule on DC migration, and selecting the molecule if it increases DC migration. Such a screening method is disclosed for Mcoln-1 in US2003/064363. In addition, methods for screening modulators of cation channel have been disclosed and can be easily adapted by the person skilled in the art to Mcoln-1, especially for TRPM4b in WO 2004/039941; for TRPM5 in WO 2004/076632; for TRPM7 in WO2007/041687 and in WO2011/072275; for TRPM4 in WO2007/140308; and for TRPM8 in WO2006/029142.

In a second aspect, the present invention relates to a Mcoln-1 inhibitor or blocker that is capable to decrease cell migration in vivo. In this context, the present invention relates to a Mcoln-1 inhibitor or blocker to be used to decrease cell migration, to the use of a Mcoln-1 inhibitor or blocker for the preparation of a drug that decreases cell migration, or a method to decrease cell migration, wherein a Mcoln-1 inhibitor or blocker is administered to a subject, preferably a therapeutically effective amount thereof.

The Mcoln-1 inhibitor can be used for treating any disease or disorder that can have a therapeutic benefit from a decreased cell migration. By "decrease" is intended to refer to a cell migration that is decreased by at least 10, 20, 30, 40 or 50% when compared to a cell migration measured in the absence of the Mcoln-1 inhibitor or blocker. By cell migration can be intended cell velocity, the percentage of migrating cells or a combination of these two criteria. Cell migration can be determined by any method known by the person skilled in the art, for instance by a method using microchannel as detailed in Faure-Andre et al for measuring the velocity (Faure-Andre et al, 2008, Science, 322, 1705-10). The terms "inhibitor", "blocker" and "antagonist" can be used and are interchangeable.

In a preferred aspect, the cell is a cancer or tumor cell. Indeed, cancer-derived metastases are highly migratory. As cancer cells share migration properties with leukocytes, and in particular with DCs, a Mcoln-1 inhibitor can be used to prevent metastasis and cancer dissemination.

In this context, the present invention relates to a Mcoln-1 inhibitor for use to treat cancer, in particular to prevent metastasis and cancer dissemination, or to the use of a Mcoln-1 inhibitor for the manufacture of a drug for treating cancer, in particular for preventing metastasis and cancer dissemination. It further relates to a method for treating cancer, comprising administering to a subject a therapeutically efficient amount of a Mcoln-1 inhibitor, thereby preventing metastasis and cancer dissemination.

The Mcoln-1 inhibitor can be used in combination with an additional drug. Accordingly, the present invention relates to:

a pharmaceutical composition comprising a Mcoln-1 inhibitor, and optionally a pharmaceutically acceptable carrier, in particular for use in the treatment of cancer, in particular for preventing metastasis, optionally in combination with radiotherapy or an anti-tumoral agent;

a Mcoln-1 inhibitor, and optionally a pharmaceutically acceptable carrier, for use in the treatment of cancer, in particular for preventing metastasis, optionally in combination with radiotherapy or an anti-tumoral agent;

the use of a Mcoln-1 inhibitor for the manufacture of a medicament for the treatment of cancer, in particular for preventing metastasis, optionally in combination with radiotherapy or an anti-tumoral agent;

a method for treating a cancer in a subject in need thereof, in particular for preventing metastasis, comprising administering an effective amount of a pharmaceutical composition comprising a Mcoln-1 inhibitor and optionally a pharmaceutically acceptable carrier;

a combined preparation, product or kit containing (a) a Mcoln-1 inhibitor and (b) an anti-tumoral agent as a combined preparation for simultaneous, separate or sequential use, in particular in the treatment of cancer, in particular for preventing metastasis;

a method for treating cancer, in particular for preventing metastasis, in a subject in need thereof, comprising administering an effective amount of a pharmaceutical composition comprising a Mcoln-1 inhibitor, and an effective amount of a pharmaceutical composition comprising an anti-tumoral agent; and a method for treating cancer, in particular for preventing metastasis, in a subject in need thereof, comprising administering an effective amount of a pharmaceutical composition comprising a Mcoln-1 inhibitor in combination with radiotherapy.

In a particular embodiment, the cancer is selected from a carcinoma, a sarcoma, a leukemia, a lymphoma, a blastoma and a melanoma, preferably a sarcoma, carcinoma and melanoma. The cancer is preferably a solid tumor or a hematopoietic malignancy. For instance, the cancer may be selected from the non-exhaustive list comprising chronic myeloid leukemia, acute lymphoblastic leukemia, Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), or chronic lymphocytic leukemia. More preferably, the cancer is selected from the list consisting of lung cancer, breast cancer, melanoma, colon and/or rectum cancer, renal cancer, prostate cancer, pancreas cancer and cervix/ovary cancer.

In a preferred embodiment, the cancer is a cancer with high probability or risk of metastasis. In particular, it could be a primary cancer associated with lymph node invasion by tumor cells.

In a more general aspect, the present invention relates to a Mcoln-1 inhibitor for use as a drug or to the use of a Mcoln-1 inhibitor for the manufacture of a drug, or a pharmaceutical composition comprising a Mcoln-1 inhibitor.

Within the context of the invention, the term "treatment" denotes curative, symptomatic, and preventive treatment. Pharmaceutical compositions and preparations of the invention can be used in humans with existing cancer or tumor(s), preferably at late stages of progression of the cancer. The pharmaceutical compositions and preparations of the invention will not necessarily cure the patient who has the cancer but will delay or slow the progression or prevent further progression of the disease, ameliorating thereby the patients' condition. In particular, the pharmaceutical compositions and preparations of the invention reduce the development of tumors and/or prevent metastasis occurrence and cancer relapse. In treating the cancer, the pharmaceutical composition of the invention is administered in a therapeutically effective amount.

By "effective amount" it is meant the quantity of the pharmaceutical composition of the invention that prevents, removes or reduces the deleterious effects of cancer in mammals, including humans. It is understood that the administered dose may be adapted by those skilled in the art according to the patient, the pathology, the mode of administration, etc. More particularly, by "therapeutically efficient amount of a Mcoln-1 inhibitor" is intended the amount that is sufficient to decrease the occurrence of metastasis.

The Mcoln-1 inhibitor can be any molecule capable of inhibiting or decreasing Mcoln-1 activity. Mcoln-1 activity can be determined by any method known by the person skilled in art for instance, in Shen et al., 2011, Nat. Comm., 3, 731. Preferably, a Mcoln-1 inhibitor is a molecule capable of decreasing the activity of Mcoln-1 by at least 10, 20, 30, 40 or 50% when compared to the activity in the absence of the molecule. The terms "inhibitor", "blocker" and "antagonist" can be used and are interchangeable. The activity can be measured for instance by measuring the calcium permeability of lysosomes.

The Mcoln-1 inhibitor can be selected from the group consisting of an antibody directed against Mcoln-1 and having an antagonist activity, an oligonucleotide inhibiting or decreasing the expression of Mcoln-1 such as antisense, siRNA or shRNA, an aptamer specific to Mcoln-1 and having an antagonist activity, a Calcium channel blocker specific to Mcoln-1, a peptide or a small molecule inhibiting or blocking Mcoln-1 such as ML-SI1, ML-SI2 and ML-SI3, Sphingomyelins, or verapamil.

In a preferred embodiment of the invention, the Mcoln-1 inhibitor is a nucleic acid molecule interfering specifically with Mcoln-1 expression, thereby decreasing or suppressing the expression of this protein. Such nucleic acids are more amply detailed below. Preferably, this nucleic acid is selected from the group consisting of a RNAi, an antisense nucleic acid or a ribozyme. Said nucleic acid can have a sequence from 15 to 50 nucleotides, preferably from 15 to 30 nucleotides. By a "decrease" in expression is meant, for example, a decrease of 30%, 40%, 50%, 70%, 80%, 90% or 95% of the gene expression product.

The term "RNAi" or "interfering RNA" means any RNA that is capable of down-regulating the expression of the targeted protein. It encompasses small interfering RNA (siRNA), double-stranded RNA (dsRNA), single-stranded RNA (ssRNA), micro-RNA (miRNA), and short hairpin RNA (shRNA) molecules. RNA interference designates a phenomenon by which dsRNA specifically suppresses expression of a target gene at post-translational level. In normal conditions, RNA interference is initiated by double-stranded RNA molecules (dsRNA) of several thousands of base pair length. In vivo, dsRNA introduced into a cell is cleaved into a mixture of short dsRNA molecules called siRNA. The enzyme that catalyzes the cleavage, Dicer, is an endo-RNase that contains RNase III domains (Bernstein et al., 2001). In mammalian cells, the siRNAs produced by Dicer are 21-23 bp in length, with a 19 or 20 nucleotide duplex sequence, two-nucleotide 3' overhangs and 5'-triphosphate extremities (Elbashir et al., 2001a; Elbashir et al., 2001b; Zamore et al., 2000). A number of patents and patent applications have described, in general terms, the use of siRNA molecules to inhibit gene expression, for example, WO 99/32619, US 20040053876, US 20040102408 and WO 2004/007718.

The Mcoln-1 inhibitor can be a silencing oligonucleotide such as siRNA or a shRNA, for instance a commercially available siRNA or a shRNA (i.e., Qiagen Cat # S100126861, S100126868, S1030577474, S10500768, S105010775, S103095148; Sigma-Aldrich Cat #). In a particular embodiment, the siRNA can be selected from the group consisting of TRPML1 si3 (SEQ ID NO: 1) or TRPML1 si5 (SEQ ID NO: 2).

Antisense nucleic acids can also be used to down-regulate the expression of Mcoln-1. The antisense nucleic acid can be complementary to all or part of a sense nucleic acid encoding Mcoln-1 e.g., complementary to the coding strand of a double-stranded cDNA molecule or complementary to an mRNA sequence, and is thought to interfere with the translation of the target mRNA. Preferably, the antisense nucleic acid is an RNA molecule complementary to a target mRNA encoding Mcoln-1.

The Mcoln-1 inhibitor can be a small molecule. Small molecules refer in particular to small organic molecules with a molecular mass <1000 Da. Small molecules and other drug candidates can readily be obtained, for example, from combinatorial and natural product libraries and using methods known in the art, or screening methods for their Mcoln-1 antagonizing activity. Furthermore, random peptide libraries, consisting of all possible combinations of amino acids, attached to a solid phase or in solution, may also be used to identify peptides that act as antagonists.

For instance, the Mcoln-1 inhibitor can be also selected from the non-exhaustive list comprising ML-SI1, ML-S12 and ML-S13 (Samie et al, 2013, Developmental Cell, 26, 511-524), Sphingomyelins (Shen et al, 2011, Nat. Comm., 3, 731), and verapamil.

The Mcoln-1 inhibitor can be a peptide, in particular a peptide fragment from Mcoln-1 inhibitor having an inhibitory effect.

The antibody directed against Mcoln-1 and having an antagonist activity can be for instance prepared by the following method comprising immunizing a non-human mammal with a composition comprising human Mcoln-1 or an immunogenic fragment thereof; optionally selecting an antibody that binds to Mcoln-1 or the immunogenic fragment thereof, and selecting an antibody that decreases the activity of Mcoln-1.

For aptamers and Spiegelmers, similar methods can be used in order to select aptamers and Spiegelmers. These methods are well-known by the person skilled in the art. As used here, the term "aptamer" means a molecule of nucleic acid or a peptide able to bind Mcoln-1. It refers to a class of molecule that represents an alternative to antibodies in terms of molecular recognition. Aptamers are oligonucleotide or oligopeptide sequences with the capacity to recognize virtually any class of target molecules with high affinity and specificity.

Such ligands may be isolated through Systematic Evolution of Ligands by EXponential enrichment (SELEX) of a random sequence library, as described in Tuerk, C. and Gold, L., Science, 1990, 249(4968):505-10. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., Clin. Chem., 1999, 45(9):1628-50.

Peptide aptamers consist of a conformationally constrained antibody variable region displayed by a platform protein, such as *E. coli* Thioredoxin A that are selected from combinatorial libraries by two hybrid methods (Colas et al., Nature, 1996, 380, 548-50).

Spiegelmers have been disclosed for instance in WO 98/08856. They are molecules similar to aptamers. However, Spiegelmers consist either completely or mostly of L-nucleotides rather than D-nucleotides in contrast to aptamers. Otherwise, particularly with regard to possible lengths of Spiegelmers, the same applies to Spiegelmers as outlined in connection with aptamers.

More generally, the present invention further relates to a method for selecting or identifying a molecule suitable for decreasing or preventing cell migration, in particular DC migration, comprising determining the effect of a molecule on the activity of Mcoln1 and selecting the molecule if it decreases or blocks the activity of Mcoln1. The method may further comprise a step of determining the effect of the selected molecule on the DC migration or velocity, and selecting the molecule if it decreases or blocks the DC migration or velocity. Such a screening method is disclosed for Mcoln-1 in US2003/064363. In addition, methods for screening modulators of cation channel have been disclosed and can be easily adapted by the person skilled in the art to Mcoln-1, especially for TRPM4b in WO 2004/039941; for TRPM5 in WO 2004/076632; for TRPM7 in WO2007/041687 and in WO2011/072275; for TRPM4 in WO2007/140308; for TRPM3 in WO2010/149614; for TRPM8 in WO2006/029142.

The Mcoln-1 inhibitor can be used in combination with another antitumoral treatment. The antitumoral agent can be an antitumoral chemotherapy, immunotherapy or hormone therapy. As used herein, the term "chemotherapy" refers to a cancer therapeutic treatment using chemical or biochemical substances, in particular using one or several antineoplastic agents. The term "immunotherapy" refers to a cancer therapeutic treatment with therapeutic antibodies. In particular, antibodies are directed against specific antigens such as the unusual antigens that are presented on the surfaces of tumors. As illustrating example, one can cite Trastuzumab or Herceptin antibody that is directed against HER2 and approved by FDA for treating breast cancer. Preferably, therapeutic antibodies function to deplete tumor cells in a patient. In particular, therapeutic antibodies specifically bind to antigens present on the surface of the tumor cells, e.g. tumor specific antigens present predominantly or exclusively on tumor cells. Alternatively, therapeutic antibodies may also prevent tumor growth by blocking specific cell receptors. The term "hormone therapy" refers to a cancer treatment having for purpose to block, add or remove hormones. For instance, in breast cancer, the female hormones estrogen and progesterone can promote the growth of some breast cancer cells. So, in these patients, hormone therapy is given to block estrogen and a non-exhaustive list commonly used drugs includes Tamoxifen, Fareston, Arimidex, Aromasin, Femara, Zoladex/Lupron, Megace, and Halotestin.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethylacetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

Pharmaceutical compositions according to the invention can comprise one or more molecules of the present invention associated with pharmaceutically acceptable excipients and/or carriers. These excipients and/or carriers are chosen according to the form of administration as described above.

Further aspects and advantages of this invention are disclosed in the following Examples section, which should be regarded as illustrative and not limiting the scope of this application.

Motility of immature or mature (LPS treated) DCs was analyzed by time-lapse imaging. Cell velocity analysis is shown in (A), and velocity variations in (B). Immature TRPML1 KO cells are less motile than their TRPML1 WT counterpart (cell velocity reduced by approximately 20%). The same tendency was observed for LPS-activated cells, where TRPML1 KO LPS cells were 20% less motile than their WT LPS counterpart. LPS-induced maturation increases cell velocity in both TRPML1 WT and KO cells (30% for TRPML1 WT LPS compared to TRPML1 WT; 20% for TRPML1 KO LPS compared to TRPML1 KO). Together these results indicate that TRPML1 is required for fast motility phases. LPS treated TRPML1 KO cells display velocity variations similar to immature TRPML1 WT cells, indicating that these cells are less persistent compared to their TRPML1 WT LPS counterpart. (Box plots indicating medians and 10-90 percentiles; 200 to 300 cells per condition, one representative experiment out of 3; ***P<0.0001, Kruskal-Wallis test.) (C) Flow cytometry analysis shows that TRPML1 KO cells are activated upon LPS treatment (CD86 levels).

Figure 1:
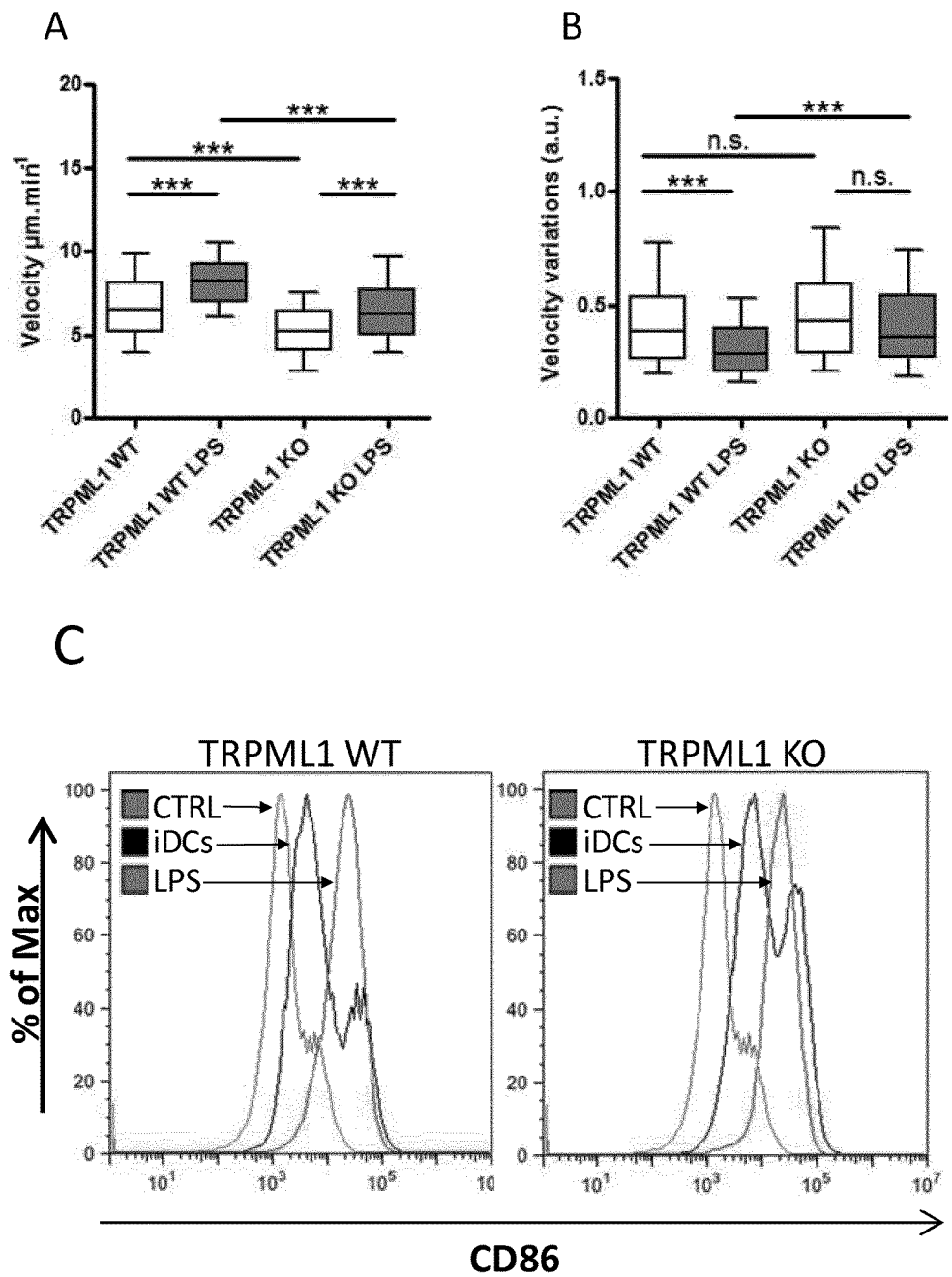
FIG. 1: TRPML1 (Mcoln-1) knock out DCs display altered motility and persistence

FIG. 2: TRPML1 (Mcoln-1) knock down DCs display altered motility and persistence (A) qPCR identification of TRPML1 siRNA leading to an efficient knock-down (KD) of TRPML1. All results were normalized to GAPDH levels. Both TRPML1 si3 and 5 were selected (reduction of TRPML1 gene expression by approximately 60%). (B) Nucleofection does not activate the cells, nor prevent the LPS-induced maturation. Shown are CD86 levels of all-star negative control (AS) and TRPML1 si5 cells, either immature or mature (LPS treated). Velocity analysis of siRNA nucleofected cells is shown in (C), and in (D) their velocity variations. TRPML1 KD cells behave similarly to TRPML1 KO cells (see FIGS. 1, C and D). (Box plots indicating medians and 10-90 percentiles; 100 to 300 cells per conditions, pool of two independent experiments; *P=0.05, ***P<0.0001, Kruskal-Wallis test).

FIG. 3: TRPML1 regulates actin dynamics in activated DCs (A) Density maps of polymerized actin in immature or mature AS-expressing (control) and in immature or mature TRPML1 si5 cells. (B) Fraction of time spent by the cells with actin at the front. In both control and TRPML1-silenced immature cells, polymerized actin is mainly found at the DC front (approximately 70% of the time for both). Mature control cells display actin polymerization at the cell center/cell rear (actin could be detected only 30% of the time at the cell front); such actin polymerization at the cell center/cell rear has been shown to be required for fast motility in mature DCs. This actin polymerization at the cell center/rear was less observed in TRPML1 si5 LPS cells, actin still being polymerized at the cell front (50% of the time). (Density maps and quantification realized on approximately 20 cells per condition, one representative experiment out of 2, **P=0.005, Kruskal-Wallis test.)

FIG. 4: TRPML1 is required for efficient migration of activated DCs to lymph node (A) Fluorescently-labeled TRPML1 WT and KO LPS DCs were co-injected into the footpad of C57BL/6 recipient mice. Popliteal lymph nodes were collected and analyzed approximately 16 h after footpad injection. The presence of migrating DCs is displayed as a percentage of total LN cells (each dot represents one mouse, two independent experiments, ***P<0.0001). (B) Example of a lymph node flow cytometry analysis, displaying TRPML1 WT LPS labeled with CMTMR, and TRPML1 KO LPS labeled with CFSE. Lower numbers of TRPML1 KO-deficient LPS DCs compared to WT LPS cells were found in the lymph node of recipient mice (approximately two times less).

Figure 5:
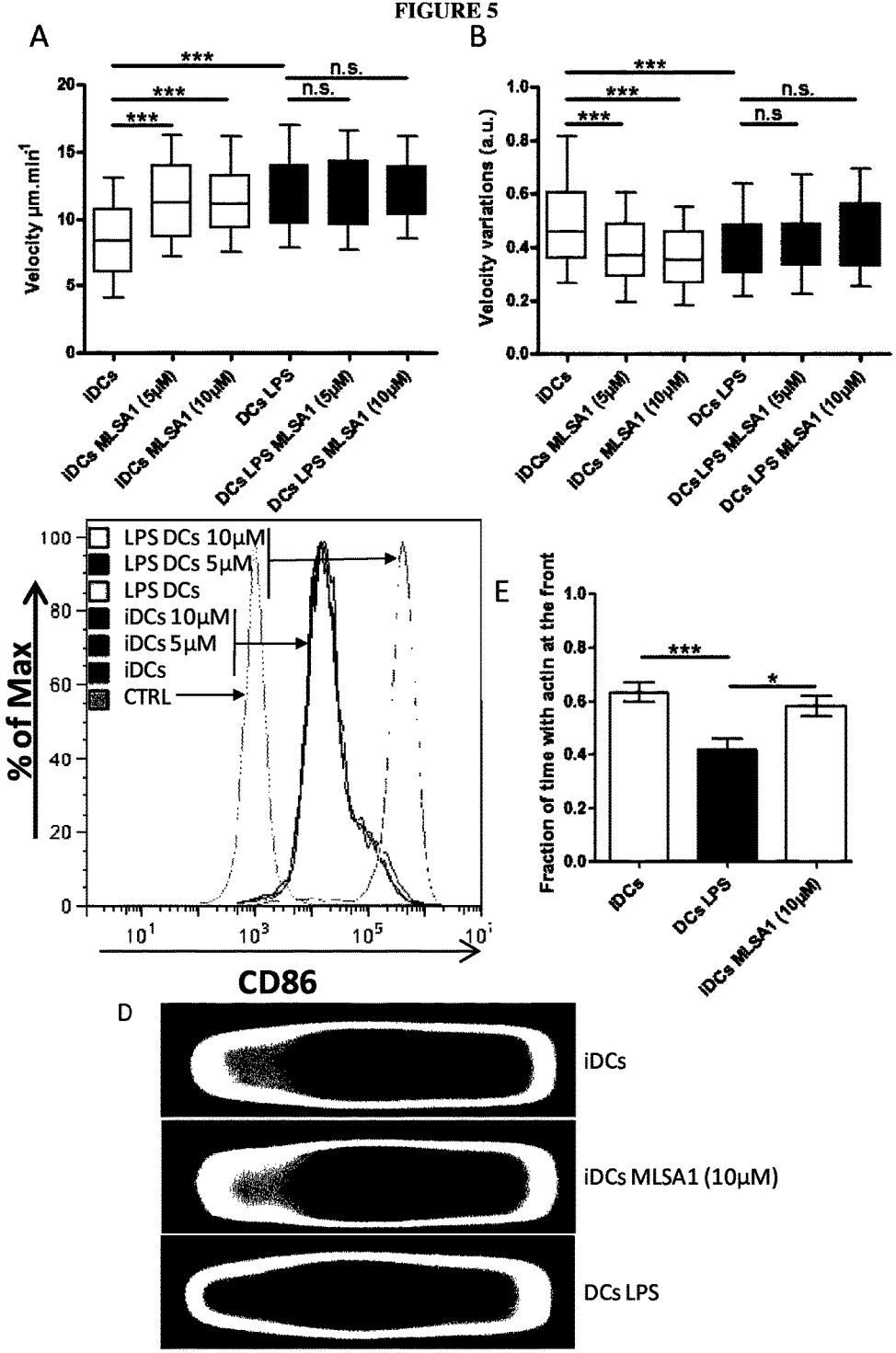

FIG. 5: TRMPL1 activation via MLSA1 in immature cells increases cell motility

MLSA1 treatment of immature cells increases both cell velocity (A) and persistence (B), to a level similar to those of mature LPS cells. Treatment of mature cells (LPS DCs) with this compound does not further increase cell velocity or their persistence. (C) MLSA1 treatment does not activate immature cells, nor prevent the LPS-induced maturation. CD86 levels of immature cells and of LPS-matured cells are shown in the absence or presence of two doses of MLSA1 (5 or 10 µM).

(D) Density maps of polymerized actin in immature DCs treated or not with MLSA1, and in mature LPS treated cells. (E) Fraction of time spent by the cells with actin at the front. MLSA1 treatment of immature DCs partially induces actin polymerization at the cell center/cell rear. The t fraction of time spent by DCs with actin at their front is decreased as compared to immature control DCs, suggesting that TRPML1 activation induces actin recruitment at the cell rear. (Density maps and quantification realized on approximately 60 cells per condition, one representative experiment out of 2, *P=0.05, ***P<0.0001, Kruskal-Wallis test.)

Figure 6:
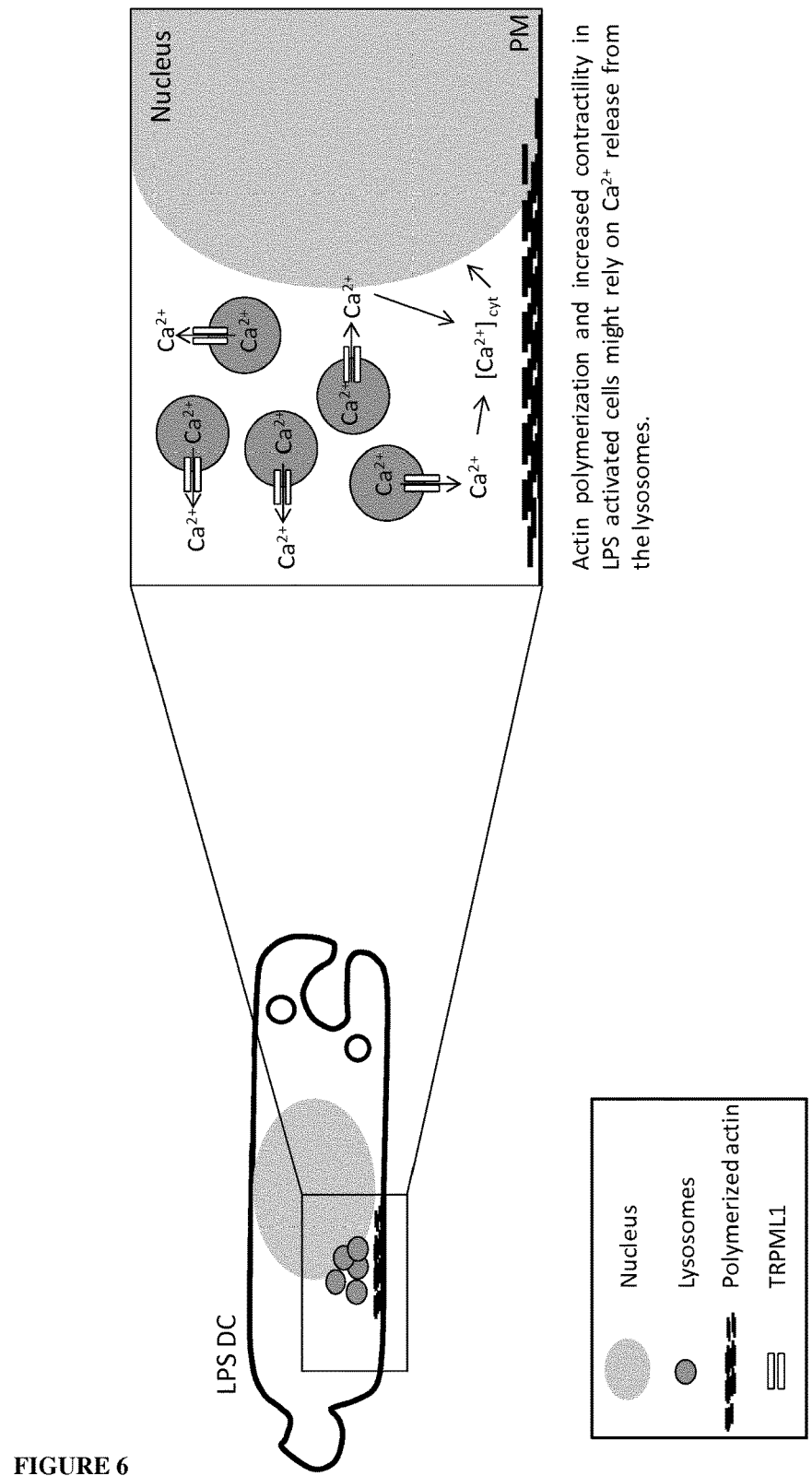

FIG. 6: Working model

TRPML1 is a transmembrane $Ca^{2+}$ channel, mostly found in the lysosomes, which allows $Ca^{2+}$ release from the lysosomes to the cytosol. In LPS-matured DCs, fast motility is linked to formin-mediated actin polymerization at the cell center/cell rear (Vargas et al. In preparation). The actin cables generated by these formins are decorated with myosin II, allowing an increased motility of mature cells. We hypothesized that $Ca^{2+}$ release from the lysosomes lead to a local $Ca^{2+}$ increase, hence (1) favoring formin-mediated actin polymerization at the cell rear, and (2) increasing cell contractility via myosin II activation.

Figure 7:
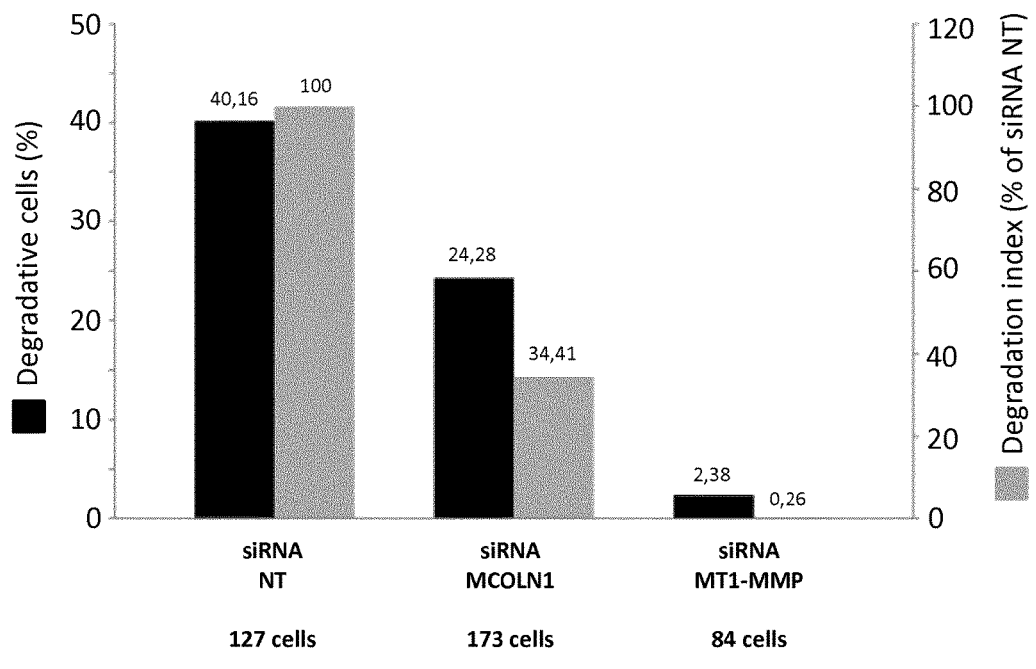

FIG. 7: Fluorescent Gelatin Degradation Assay, Effect of MCOLN1 silencing

EXAMPLES

Results

TRPML1 (Mcoln-1)-Deficient or -Silenced Dendritic Cells Display Altered Motility and Persistence To investigate whether TRPML1 plays a role in dendritic cell (DC) migration, the inventors differentiated DCs from the bone-marrow of TRPML1-deficient and -sufficient mice and analyzed their ability to migrate along micro-channels (5×5 µm) prior to and after LPS treatment. They observed that LPS-activated DCs displayed increased velocity and migration persistence (FIGS. 1A and B), in agreement with the previous findings of the inventors. Strikingly, the velocity of TRPML1 knock out DCs and their migration persistence was decreased, indicating that this lysosomal calcium channel is required for DCs to reach their maximal speed and migrate directionally. Importantly, no effect of TRPML1 on DC maturation was observed, as shown by normal levels of surface CD86 expression (FIG. 10). Equivalent results were obtained when analyzing the migration of TRPML1-silenced DCs in micro-channels (FIG. 2). In addition, transfer of TRPML1 control and knock out DCs into the footpad of wild-type recipients showed impaired arrival of TRPML1-deficient cells from the footpad to the popliteal lymph node after 24 h (FIG. 3). The inventors conclude that TRPML1 deficiency leads to impaired DC migration ex vivo and in vivo.

TRPML1 (Mcoln-1) Regulates Actin Dynamics in Activated Dendritic Cells

To investigate the molecular mechanisms involved in the regulation of DC migration by TRPML1, the inventors silenced it in DCs derived from LifeAct transgenic mice (Riedl et al., 2010, Nat. Methods, 7, 168-169) and analyzed their actin dynamics during migration. As previously observed, the inventors found that polymerized actin was mainly enriched at the cell front in immature DCs, whereas it rather concentrated at the cell rear in activated DCs (FIGS. 4A and B). Noticeably, TRPML1 silencing modified actin localization in wild-type activated DCs, which exhibited most of their actin at their front. The inventors conclude that TRPML1 promotes the migration of activated DCs most likely by allowing or stabilizing actin polymerization at their rear, which is required for their fast and persistent locomotion.

TRMPL1 Activation Via MLSA1 in Immature Cells Increases Cell Motility

To strengthen these results, the inventors analyzed DC migration in micro-channel upon treatment with the drug MLSA1, which was shown to activate TRPML1 (Shen et al., 2012, Nat. Comm., 3:731). Remarkably, MLSA1 increased the speed and persistence of immature DCs to the levels measured in activated cells, indicating that this lysosomal calcium channel is most likely responsible for their enhanced locomotion (FIGS. 5A and B). No effect of MLSA1 on DC maturation was observed (FIG. 5C). In addition, analysis of actin dynamics in MLSA1-treated immature DCs showed that actin was enriched at their rear, consistent with their fast and persistent migratory phenotype (FIGS. 5D and E). Hence, TRPML1 facilitates DC migration by promoting the enrichment of polymerized actin at their cell rear but without altering their maturation (see model on FIG. 6).

Fluorescent Gelatin Degradation Assay: Effect of MCOLN1 silencing 40.2% MDA-MB-231 degraded FITC-gelatin when treated with the control siRNA (NT) whereas only 2.4% MDA-MB-231 degraded FITC-gelatin when treated with the MT1-MMP siRNA (MT1-MMP is the enzyme responsible for the degradation). When the cells were treated with MCOLN1 siRNA, 24.3% MDA-MB-231 degraded FITC-gelatin. This result suggests that the silencing of MCOLN1 inhibits 40% of the degradative capabilities of MDA-MB-231, thereby illustrating the capacity of MCOLN1 inhibitor to prevent or decrease tumoral cell migration.

Materials and Methods

Antibodies and Reagents

The following reagents were used for imaging experiments: WGA AlexaFluor-647 and Hoechst (both from Life Technologies). Micro-channels were coated with Fibronectin (Sigma). Cell activation was performed with LPS (Sigma). For flow cytometry the following antibodies were used: anti-CD86 (GL1 clone, 553692) and a Rat IgG$_{2a,\kappa}$ isotype control (553930) from BD Biosciences.

Mice

Lifeact-GFP knock-in (referred to as Lifeact), and TRPML1 knock-out mice were previously described (Riedl et al., 2010, Nat. Methods, 7, 168-169 Chandra et al., Gastroenterology, 2011, 140, 857-867).

Cells

Mouse bone-marrow cells were cultured during 10-12 days in medium supplemented with fetal calf serum and granulocyte-macrophage colony stimulating factor-containing supernatant obtained from transfected J558 cells, as previously described (Faure-Andre et al, 2008, Science, 322, 1705-10). For migration or mapping assays (see below), cells at day 10-12 were activated with 100 ng/ml of LPS (mature cells, LPS DCs), for 30 min, then rinsed 3 times with complete media and put into the channels. Counterpart immature cells for these experiments are treated in the same condition, but in absence of LPS.

Electroporation

For siRNA-mediated gene silencing, Lifeact cells were cultured for 7 days, and then transfected with either a siRNA directed against mouse TRPML1 (Mm_Mcoln1_3 referred to as TRPML1 si3 (target sequence 5'-CACCATCCACT-TCCAGCTGAA-3' (SEQ ID NO: 1)), or Mm_Mcoln1_5, referred to as TRPML1 si5 (target sequence: 5'-TA-CAAGAACCTCACACTGAAA-3' (SEQ ID NO: 2))) or a control non-targeting all-star siRNA (all from Qiagen GmbH).

Electroporation were performed with Amaxa Mouse Dendritic Cell Nucleofector Kit (VPA-1011), according to the manufacturer protocol (Lonza). Briefly, bone marrow derived cells ($3*10^6$) are resuspended into 100 μl of Amaxa supplemented buffer with 1 μM of siRNA and nucleofected using the program Y-001 (Amaxa Nucleofector, Lonza). Cells were immediately transferred into 6 well plates with pre-warmed media. Cells were used for experiments 3 days after nucleofection.

qPCR

Dendritic cells (at least $1\times10^6$ cells) were collected prior to experiments, and total mRNA were extracted according to the manufacturer protocol (Nucleospin RNA II, Macherey-Nagel). Complementary DNA were synthesized from 1 μg of total RNA, using the superscript vilo reverse kit (Invitrogen). QPCR were performed using the Taqman Gene expression master mix, and the best coverage primer sets Mm00522550_m1 and Mm99999915_g1 for TRPML1, and GAPDH, respectively (all from Applied Biosystems, Life technologies). All experiments were performed on a Roche lightcycler (Roche). Expression levels of TRPML1 gene was calculated using the $2^{-\Delta\Delta CT}$ method, using GAPDH expression levels as an endogenous control.

Flow Cytometry Analysis

Cells were resuspended in staining buffer (PBS BSA 2%) and stained 30 min at 4° C. with the indicated antibodies. Cells were then washed 3 times and resuspended in staining buffer. All Facs experiments were carried on an Accuri flow cytometer (BD Biosciences).

Preparation of Micro-Channels

Micro-channels were prepared as previously described (Faure-Andre et al, 2008, Science, 322, 1705-10; Heuze et al., 2011, Methods Mol Biol., 769, 415-434). They were incubated with 10 μg/ml fibronectin alone for 1 h and washed with PBS.

Migration Assay

For migration assay, cells were loaded in micro-channels (section 5×5 μm) and imaged at least for 16 hours on an epifluorescence video-microscope Nikon TiE microscope equipped with a cooled CCD camera (HQ2, Photometrics)

with a 10× objective, one transmission phase image taken every 2 minutes. Kymograph extraction and instantaneous velocity analysis were performed using a homemade program as described previously (Faure-Andre et al, 2008, Science, 322, 1705-10).

Mapping Assay

Lifeact dendritic cells (nucleofected or not) were incubated for 30 min in 200 ng/l Hoechst-containing medium, washed 3 times and $10^5$ cells per well were loaded and incubated from 4 h to overnight to allow their entry into micro-channels (section was 8×5 µm). After entry, cells were imaged at least for 16 hours on an epifluorescence video-microscope Nikon TiE microscope equipped with a cooled CCD camera (HQ2, Photometrics) with a 20× objective. Images were acquired every 3 minutes. Image processing was performed with ImageJ software (ref: Rasband, W. S. ImageJ, U.S. National Institutes of Health, Bethesda, Md., USA, imagej.nih.gov/ij/, 1997-2012). Cells moving in micro-channels were segmented by automatic thresholding method (Triangle) on the actin channel. For each time-point, the smallest rectangle containing the cell was defined and images were cropped. Then, cropped images were normalized in size and the mean actin image of each cell (average pixel intensity for all time-points) was computed. All mean actin images were normalized in intensity and averaged to obtain the mean polymerized actin distribution of the experiment. Furthermore for each cell, spatial coordinates of the nuclei were measured and ratio between the mean actin density at the front and at the back of the nucleus was computed. Velocities of cells were estimated according to these spatial coordinates.

Migration of Dendritic Cells from the Footpad to the Lymph Node

Experiments were realized as described previously (Faure-Andre et al, 2008, Science, 322, 1705-10).

Fluorescent Gelatin Degradation

The human breast cancer adenocarcinoma cell line MDA-MB-231 was transfected with 50 nM control NT siRNA, MCOLN1 siRNA (Smart pool siRNA from Dharmacon, L-006281-00-0010, ON-TARGETplus Human MCOLN1 (57192) siRNA-SMARTpool, 10 nmol. siRNA J-006281-05+siRNA J-006281-06+siRNA J-006281-07+siRNA J-006281-08, Target sequences of SEQ ID NOs: 3-5) or MT1-MMP siRNA using Lullaby reagent (OZ Biosciences). 72 h after treatment, cells were incubated for 5 h on FITC-conjugated cross-linked gelatin (Invitrogen) as described previously (Sakurai-Yageta et al., 2008, J. Cell. Biol., 181, 985-998) and then fixed and stained for F-actin and cortactin. Cells were imaged with the 63× objective of a wide-field microscope (DM6000 B/M; Leica) and the quantification of gelatin degradation was achieved using MetaMorph as described previously (Monteiro et al. 2013, J. Cell. Biol., 203, 1063-1079).

The invention claimed is:

1. A method of modulating cell migration comprising contacting a dendritic cell expressing mucolipin-1 (Mcoln-1) with a small molecule having molecular mass of less than 1000 Da that is selected from ML-SA1, SF-22 and SF-51 and that modulates Mcoln-1 and, thereby, modulates dendritic cell migration.

2. The method according to claim 1, wherein the small molecule is an activator of Mcoln-1 and thereby cell migration is enhanced.

3. The method of claim 1, said method comprising the administration of the small molecule that activates Mcoln-1 to a subject, thereby stimulating migration of dendritic cells in said subject and administering a vaccine to said subject.

4. The method of claim 1, said method comprising administering the small molecule that activates Mcoln-1 to said subject, thereby stimulating migration of dendritic cells in a subject having an autoimmune disease.

5. The method of claim 1, said method comprising administering the small molecule that activates Mcoln-1 to a subject having an infection, thereby stimulating migration of dendritic cells in said subject.

* * * * *

UNITED STATES PATENT AND TRADEMARK OFFICE
CERTIFICATE OF CORRECTION

PATENT NO. : 10,100,313 B2
APPLICATION NO. : 15/116848
DATED : October 16, 2018
INVENTOR(S) : Ana-Maria Lennon-Dumenil, Pablo Vargas and Marine Bretou It is certified that error appears in the above-identified patent and that said Letters Patent is hereby corrected as shown below:

On the Title Page

Column 2, after item (57) replace "5 Claims, 6 Drawing sheets" with --4 Claims, 6 Drawing Sheets--.

In the Specification

Column 10,
Lines 30-31, "S100126861, S100126868, S1030577474, S10500768, S105010775, S103095148" should read --SI00126861, SI00126868, SI030577474, SI0500768, SI05010775, SI03095148--.

Column 10,
Lines 56-57, "ML-S12 and ML-S13" should read --ML-SI2 and ML-SI3--.

Column 15,
Line 3, "(FIG. 10)" should read --(Fig. 1C)--.

In the Claims

Column 19, Lines 28-39 and Column 20, Lines 28-37:
"1. A method of modulating cell migration comprising contacting a dendritic cell expressing mucolipin-1 (Mcoln-1) with a small molecule having molecular mass of less than 1000 Da that is selected from ML-SA1, SF-22 and SF-51 and that modulates Mcoln-1 and, thereby, modulates dendritic cell migration.
2. The method according to claim 1, wherein the small molecule is an activator of Mcoln-1 and thereby cell migration is enhanced.
3. The method of claim 1, said method comprising the administration of the small molecule that activates Mcoln-1 to a subject, thereby stimulating migration of dendritic cells in said subject and administering a vaccine to said subject.
4. The method of claim 1, said method comprising administering the small molecule that activates Mcoln-1 to said subject, thereby stimulating migration of dendritic cells in a subject having an Signed and Sealed this
Eighth Day of October, 2019

Andrei Iancu
*Director of the United States Patent and Trademark Office*

CERTIFICATE OF CORRECTION (continued)
U.S. Pat. No. 10,100,313 B2 autoimmune disease.

5. The method of claim 1, said method comprising administering the small molecule that activates Mcoln-1 to a subject having an infection, thereby stimulating migration of dendritic cells in said subject."

Should read:

--1. A method of modulating cell migration comprising contacting a dendritic cell expressing mucolipin-1 (Mcoln-1) with a small molecule having molecular mass of less than 1000 Da that is selected from ML-SA1, SF-22 and SF-51 and that modulates Mcoln-1 and, thereby, modulates dendritic cell migration.

2. The method of claim 1, said method comprising the administration of the small molecule that activates Mcoln-1 to a subject, thereby stimulating migration of dendritic cells in said subject and administering a vaccine to said subject.

3. The method of claim 1, said method comprising administering the small molecule that activates Mcoln-1 to said subject, thereby stimulating migration of dendritic cells in a subject having an autoimmune disease.

4. The method of claim 1, said method comprising administering the small molecule that activates Mcoln-1 to a subject having an infection, thereby stimulating migration of dendritic cells in said subject.--.

SEQUENCE LISTING

```
<160> NUMBER OF SEQ ID NOS: 6

<210> SEQ ID NO 1
<211> LENGTH: 21
<212> TYPE: DNA
<213> ORGANISM: artificial sequence
<220> FEATURE:
<223> OTHER INFORMATION: TRPML1 si3

<400> SEQUENCE: 1
caccatccac ttccagctga a                                      21

<210> SEQ ID NO 2
<211> LENGTH: 21
<212> TYPE: DNA
<213> ORGANISM: artificial sequence
<220> FEATURE:
<223> OTHER INFORMATION: TRPML1 si5

<400> SEQUENCE: 2
tacaagaacc tcacactgaa a                                      21

<210> SEQ ID NO 3
<211> LENGTH: 19
<212> TYPE: RNA
<213> ORGANISM: artificial sequence
<220> FEATURE:
<223> OTHER INFORMATION: Mcoln-1 target sequence

<400> SEQUENCE: 3
gaccuucgcc gucgucuca                                         19

<210> SEQ ID NO 4
<211> LENGTH: 19
<212> TYPE: RNA
<213> ORGANISM: artificial sequence
<220> FEATURE:
<223> OTHER INFORMATION: Mcoln-1 target sequence
```

```
<400> SEQUENCE: 4
ugaucacguu ugacaacaa                                                                    19

<210> SEQ ID NO 5
<211> LENGTH: 19
<212> TYPE: RNA
<213> ORGANISM: artificial sequence
<220> FEATURE:
<223> OTHER INFORMATION: Mcoln-1 target sequence

<400> SEQUENCE: 5
caacgacaca uuugacauu                                                                    19

<210> SEQ ID NO 6
<211> LENGTH: 19
<212> TYPE: RNA
<213> ORGANISM: artificial sequence
<220> FEATURE:
<223> OTHER INFORMATION: Mcoln-1 target sequence

<400> SEQUENCE: 6
gaucucaccc ucuuggaaa                                                                    19
```